United States Patent [19]
Hardy et al.

[11] Patent Number: 5,339,812
[45] Date of Patent: * Aug. 23, 1994

[54] THREE-DIMENSIONAL COMPUTER GRAPHICS SIMULATION AND COMPUTERIZED NUMERICAL OPTIMIZATION FOR DOSE DELIVERY AND TREATMENT PLANNING

[75] Inventors: Tyrone L. Hardy, 13433 Camino Carmel, Del Mar, Calif. 92014; Gary W. Glover, Huntington Beach, Calif.; Laura D. Brynildson, Albuquerque, N. Mex.

[73] Assignees: Medical Instrumentation and Diagnostic Corporation; Tyrone L. Hardy, San Diego, Calif.

[*] Notice: The portion of the term of this patent subsequent to Apr. 27, 2010 has been disclaimed.

[21] Appl. No.: 989,702

[22] Filed: Dec. 14, 1992

Related U.S. Application Data

[63] Continuation of Ser. No. 534,975, Jun. 8, 1990, Pat. No. 5,205,289, which is a continuation-in-part of Ser. No. 500,788, Mar. 28, 1990, which is a continuation-in-part of Ser. No. 290,316, Dec. 23, 1988, Pat. No. 5,099,846.

[51] Int. Cl.$^5$ .................................................. A61B 6/00
[52] U.S. Cl. .................................. 128/653.1; 606/130; 600/7; 364/413.26
[58] Field of Search ...................... 128/653.1, 654, 659; 606/130; 600/1-3, 7, 8; 364/413.26

[56] References Cited

U.S. PATENT DOCUMENTS

| | | |
|---|---|---|
| 3,508,552 | 4/1970 | Hainault . |
| 3,783,251 | 1/1974 | Pavkovich . |
| 3,987,281 | 10/1976 | Hodes . |
| 4,079,450 | 3/1978 | Grimm et al. . |
| 4,123,143 | 10/1979 | Yachin et al. . |
| 4,223,227 | 9/1980 | Horwitz . |
| 4,230,117 | 10/1980 | Anichkov . |
| 4,259,725 | 3/1981 | Andrews et al. . |
| 4,278,888 | 7/1981 | Wagner . |
| 4,341,220 | 7/1982 | Perry ................................ 128/630 |
| 4,350,159 | 9/1982 | Gouda . |
| 4,386,602 | 6/1983 | Sheldon et al. . |
| 4,455,609 | 6/1984 | Inamura et al. . |
| 4,463,758 | 8/1984 | Patil . |
| 4,502,147 | 2/1985 | Michaels . |
| 4,583,538 | 4/1986 | Onik et al. . |
| 4,597,380 | 7/1986 | Raif et al. . |
| 4,598,368 | 7/1986 | Umemura . |
| 4,608,635 | 8/1986 | Osterholm . |
| 4,608,977 | 9/1986 | Brown . |
| 4,617,925 | 10/1986 | Laitenin . |
| 4,638,798 | 1/1987 | Shelden et al. . |
| 4,651,732 | 3/1987 | Frederick . |
| 4,653,112 | 3/1987 | Ouimette . |
| 4,702,571 | 10/1987 | Barber . |
| 4,706,665 | 11/1987 | Gouda . |
| 4,729,099 | 3/1988 | Iverson et al. . |
| 4,777,598 | 10/1988 | Kellar et al. . |

(List continued on next page.)

FOREIGN PATENT DOCUMENTS 2384481 10/1978 France .
1074239A 4/1982 U.S.S.R. .

OTHER PUBLICATIONS

B. Bauer-Kirpes et al., "Computerized Optimization of $^{125}$I Implants in Brain Tumors," J. Radiation Oncology Biol. Phys., vol. 13, No. 5, pp. 1013-1023 (May 1988).

(List continued on next page.)

Primary Examiner—Ruth S. Smith
Attorney, Agent, or Firm—Jeffrey D. Myers; Deborah A. Peacock; Donovan F. Duggan

[57] ABSTRACT

An optimized dose delivery system using computer graphics simulation techniques and computerized numerical optimization. A volume, such as a tumor volume, is graphically simulated and meshed with node points. The dose delivery is calculated depending upon input variables, deriving an objective function related to dose efficacy. A numerical optimization algorithm optimizes the input variables based upon such objective function.

18 Claims, 9 Drawing Sheets

U.S. PATENT DOCUMENTS

| | | |
|---|---|---|
| 4,790,026 | 12/1988 | Gennery et al. . |
| 4,791,934 | 12/1988 | Brunnett . |
| 4,813,588 | 3/1989 | Srivastava et al. .. |
| 4,832,049 | 5/1989 | Matsushita et al. . |
| 4,856,528 | 8/1989 | Yang . |
| 4,879,668 | 11/1989 | Cline et al. . |
| 4,884,566 | 12/1989 | Mountz et al. . |
| 4,905,702 | 3/1990 | Foss . |
| 4,919,516 | 4/1990 | Petran et al. . |
| 4,976,680 | 12/1990 | Hayman et al. . |
| 4,977,505 | 12/1990 | Pelizzari et al. . |
| 5,027,818 | 7/1991 | Bova et al. .......... 606/130 |
| 5,099,846 | 3/1992 | Hardy . |
| 5,205,289 | 4/1993 | Hardy et al. ......... 128/653.1 |

OTHER PUBLICATIONS

F. Colombo et al., "External Stereotactic Irradiation by Linear Accelerator," Neurosurgery, vol. 16, No. 2, pp. 154–159 (Feb. 1985).

W. Friedman et al., "The University of Florida Radiosurgery System," Surg. Neurol., vol. 32, pp. 334–342 (1989).

T. L. Hardy, "Stereotactic CT Atlases," *Modern Stereotactic Surgery*, L. D. Lunsford (ed.), Ch. 34, pp. 425–439 (1988).

T. L. Hardy et al., "CASS: A Program For Computer Assisted Stereotaxic Surgery," Proceedings of the Fifth Annual Symposium on Computer Applications in Medical Care, IEEE, pp. 1116–1126 (Nov. 1981).

T. L. Hardy et al., "Computer–Assisted Stereotactic Surgery," Proceedings of the 8th Meeting World Soc. Stereotactic and Functional Neurosurgery, Zurich 1981, *Applied Neurophysiology*, vol. 45, pp. 396–398 (1982).

T. L. Hardy et al., "A Portable Computerized Tomographic Method for Tumer Biopsy," Acta/Supplementum, No. 33, p. 444 (May 18, 1983).

T. L. Hardy et al., "Computer Graphics with Computerized Tomography for Functional Neurosurgery," Proceedings of the Amer. Soc. Stereotactic and Functional Neurosurgery, Durham, N.C. 1983, *Applied Neurophysiology*, vol. 46, pp. 217–226 (1983).

B. A. Kall et al., "Comprehensive Computer–Assisted Data Collection Treatment Planning and Interactive Surgery," SPIE, vol. 767, *Medical Imaging*, pp. 509–514 (1987).

P. J. Kelly et al., "Computer–assisted Stereotactic Laser Microsurgery for the Treatment of Intracranial Neoplasms," Neurosurgery, vol. 10, No. 3, pp. 324–331 (Mar. 1982).

P. J. Kelly et al., "Method of Computed Tomography–based Stereotactic Biopsy with Arteriographic Control," Neurosurgery, vol. 14, No. 2, pp. 172–177 (Feb. 1984).

P. J. Kelly et al., "Functional Stereotactic Surgery Utilizing CT Data and Computer Generated Stereotactic Atlas," Acta Neurochirurgica, Suppl. No. 33, pp. 577–583 (1984).

P. J. Kelly et al., "Stereotactic CT Scanning for the Biopsy of Intracranial Lesions and Functioinal Neurosurgery," Applied Neurophysiology, vol. 46, pp. 193–199 (1983).

P. J. Kelly et al., "Computer Simulation for the Stereotactic Placement of Interstitial Radionuclide Sources into Computer Tomography–defined Tumor Volumes," Neurosurgery, vol. 14, No. 4, pp. 442–448 (Apr. 1984).

M. Koslow et al., "Stereotactic Surgical System Controlled by Computed Tomography," Neurosurgery, vol. 8, No. 1, pp. 72–82 (Jan. 1981).

D. Lefkopoulos et al., "The Ill–Conditioning in Stereotaxic Irradiation," Proceedings of the 8th International Conference, Juan–les–Pins, France, pp. 1129–1140 (Jun. 8–10, 1988).

A. R. Parkinson et al., "Exploring Design Space: Optimization as Synthesizer of Design and Analysis," Computers in Mechanical Engineering, pp. 28–36 (Mar. 1985).

T. M. Peters et al., "The Role of Computer Tomographic and Digital Radiographic Techniques in Stereotactic Procedures for Electrode Implantation and Mapping, and Lesion Localization," Proc. of the Amer. Soc. Stereotactic and Functional Neurosurgery, Durham, N.C. 1983, *Appl. Neurophysiol.*, vol. 46, pp. 200–205 (1983).

R. K. Rice et al., "Measurements of Dose Distributions in Small Beams of 6MV X–Rays," Phys. Med. Biol., vol. 32, No. 9, pp. 1087–1099 (1987).

C. H. Shelden et al., "Development of a Computerized Microstereotaxis Method for Localization and Removal of Minute CNS Lesions Under Direct 3–D Vision," J. Neurosurg., vol. 52, pp. 21–27 (Jan. 1980).

OTHER PUBLICATIONS

C. J. Thompson et al., "A System for Anatomical and Functional Mapping of the Human Thalamus," Computers and Biomedical Research, vol. 10, pp. 9–24 (1977).

R. Vercillo et al., "Digital Image Review Console," Proceedings of SPIE, Newport Beach, Calif., Feb. 1–6, 1987, *Medical Imaging*, Roger H. Schneider and Samuel J. Dwyer III (Chairs/Editors), vol. 767, pp. 708–712 (1987).

K. Weaver et al., "A CT-based Computerized Treatment Planning System for I-125 Stereotactic Brain Implants," Int. J. Radiation Oncology Biol. Phys., vol. 18, No. 2, pp. 445–454 (Feb. 1990).

K. R. Winston et al., "Linear Accelerator as a Neurosurgical Tool for Stereotactic Radiosurgery," Neurosurgery, vol. 22, No. 3, pp. 454–462 (Mar. 1988).

Advertisement, "The Idea That Stereotaxy Could Bring More Precision to Microsurgery is no Longer a Possibility," Leksell Micro-Stereotactic System, distibuted by Electa Instruments AB, Stockholm Sweden, Elekta Instruments, Inc., Decatur, Ga. (1989).

Brochure, "Hardware and Software for Computer Assisted CT and MRI Based Stereotactic Neurosurgery," Stereotactic Medical Systems, Inc. designed by Patrick Kelly et al.

THREE-DIMENSIONAL COMPUTER GRAPHICS SIMULATION AND COMPUTERIZED NUMERICAL OPTIMIZATION FOR DOSE DELIVERY AND TREATMENT PLANNING

CROSS-REFERENCE TO RELATED APPLICATION

This application is a continuation of U.S. patent application Ser. No. 07/534,975, entitled Three-Dimensional Computer Graphics Simulation and Computerized Numerical Optimization for Dose Delivery and Treatment Planning, to Hardy, filed Jun. 8, 1990 now U.S. Pat. No. 5,205,289, which is a continuation-in-part application of U.S. patent application Ser. No. 07/500,788, entitled Three-Dimensional Graphics Simulation and Actual Imaging Data Composite Display, to Hardy, filed on Mar. 28, 1990, which is a continuation-in-part of U.S. patent application Ser. No. 07/290,316 now U.S. Pat. No. 5,099,846, entitled Method and Apparatus for Video Presentation from a Variety of Scanner Imaging Sources, to Hardy, filed Dec. 23, 1988, the teachings of all of which are incorporated herein by reference.

This application is also related to U.S. patent application Ser. No. 07/428,242 (abandoned), entitled Three-Dimensional Laser Localization Apparatus and Method for Stereotactic Diagnoses or Surgery, to Hardy, et al., filed Oct. 27, 1989, the teachings of which are incorporated herein by reference.

BACKGROUND OF THE INVENTION

1Field of the Invention

The present invention relates to an apparatus and method of combining three-dimensional computer graphic simulation of volumes with computerized numerical optimization by mathematical computation.

2. Description of the Related Art Including Information Disclosed under 37 C.F.R. §§1.97–1.99

Currently there are no efficient optimization techniques or treatment planning methods for optimizing the dose delivery and shape of, e.g., radiation zones in the treatment of various tumors in the body, especially the brain. Current methods involve various means of rough approximation of dose delivery to a tumor region with severe limitations on tailoring the radiation dose delivery to fit the exact dimensions and shape of the tumor volume. In addition, there is no method available which allows treatment planners to effectively minimize the dose delivery to reasonably normal brain tissue surrounding a tumor lesion and maximizing the dose to the tumor itself, other than the rather cumbersome, two-dimensional dose planning systems which rely heavily on dose volume histogram calculations. As designed, currently used systems involve very tedious iterative processing by the planner to fit a radiation treatment dose and volume distribution to a given tumor volume or such similar tissue volume. Current methods are very laborious, often requiring up to a day or more to do a single dose plan or any simple iterative adjustment. Such methods are severely limited and many dose treatment planners are constrained by current technological limitations to "closely approximate" a given dose delivery. There are various devices on the market; for example, the Leksell gamma knife (see L. Leksell, Stereotaxis and Radiosurgery: An operative system, Springfield, IL: Charles C. Thomas, 1971) and the LINAC® scalpel" (see K.R. Winston, W. Lutz, "Linear Accelerator as a Neurosurgical Tool for Stereotactic Radiosurgery," Neurosurgery, Vol. 22, No. 3, 1988; F. Colombo, A. Benedetti, et al., "External Stereotactic Irradiation by Linear Accelerator," Neurosurgery, Vol. 16, No. 2, 1985; and W.A. Friedman, F.J. Bova, "The University of Florida Radiosurgery System," Surg. Neurol., Vol 32, pp. 334–342, 1989), which are capable of delivering the dose delivery to the tumor volume and optimizing the delivery such that dose zones can be tailored to tumor shape, configuration and size. Similarly, there are currently available methods for the accurate placement of radioisotopes, contained within catheters, in strategic areas of the brain for the direct delivery of a radiation dose to a given area of the brain. This method also has similar limitations in radiation dose delivery optimization (see K. Weaver, V. Smith, et al., "AGT Based Computerized Treatment Planning System for I-125 Stereotactic Brain Implants," Int. J. of Radiation Oncology, Biol. Phys., Vol 18, pp. 445–454, 1990; P.J. Kelly, B.A. Kall, S. Goerss, "Computer Simulation for the Stereotactic Placement of Interstitial Radionuclide Sources into Computed Tomography-Defined Tumor Volumes," Neurosurgery, Vol. 14, No. 4, 1984; and B. Bauer-Kirpes, V. Sturm, W. Schlegel, and W.J. Lorenz, "Computerized Optimization of I-125 Implants in Brain Tumors," Int. J. Radiat. Oncol. Biol. Phys., Vol. 14 pp. 1013–1023, 1988).

None of the methods or devices described above combine three-dimensional graphics simulation and actual imaging data, such as disclosed in parent application, Ser. No. 07/500,788, with computerized numerical optimization for dose delivery treatment planning. Generally, co-pending applications Ser. Nos. 07/500,788 and 07/290,316 involve acquiring a magnetic resonance (MR), computed tomography (CT), or the like, image of a volume, such as a tumor volume, in serial sections through the volume, outlining such sections, and creating a three-dimensional simulation of the volume.

The concept of mathematical function optimization has existed since the advent of calculus and over the years has developed into very efficient and robust algorithms for constrained multidimensional nonlinear optimization. The word "optimization," when used in this context and in the specification and claim, means the rigorous use of algorithmic steps, implemented as computer code, to search for and find a mathematically defined local minimum (or maximum) of a given objective function. An objective function can take many forms (e.g., calculated stress in a structural member, aerodynamic loading on a wing, or a calculated dose of brain cell irradiation), but is simply a chosen measure of the desired behavior of the object, system, or process being designed. The term "constrained optimization" then refers to the optimization process, as explained above, being conducted within certain allowable limits or constraints. For example, a desired design objective may be to design a car frame of minimum weight design. If no constraints were put on this design problem, the minimum weight design would not be able to withstand the encountered loads during operation and may not even be manufacturable. Constraints are put on the design problem that require the car frame to support certain loads under various conditions and to ensure that the final design will be manufacturable given current technology. Typically, "real world" design problems are constrained by certain necessary performance criteria. Modeling the physical behavior of "real world" objects, systems, and processes requires the use of complex nonlinear mathematical equations formed from available variables and incorporated within the computer code. Therefore, using the definitions provided in this paragraph, the term "constrained multidimensional nonlinear optimization" is defined.

Such algorithms as discussed above were designed to replace the traditional "hunt and peck" process with efficient, non-random techniques for gleaning information from the computer model in the form of slopes and curvature of the objective function "hyper-surface" (a surface with three or more variables). When coupled in this manner, the algorithms take the place of the user and autonomously search and find the optimal combination of variables to maximize or minimize a desired objective.

Two robust and efficient nonlinear optimization algorithms available in the art are the Generalized Reduced Gradient (GRG) algorithm and the Sequential Quadratic Programming (SQP) algorithm. Since the algorithms themselves are in the public domain, many private versions of these algorithms are currently available as software packages.

The present invention applies these numerical optimization techniques to help improve the planning process generally for optimal dose distribution planning and specifically for the radiation treatment of brain tumors. The current techniques of radiation therapy require the designers (neurosurgeons and radiation oncologists) to perform tedious design iterations in their search for the optimal placement of radioisotope seeds and external beam trajectories. By incorporating numerical optimization algorithms into the existing framework, the operation planning process becomes virtually automatic and produces better planning designs than current techniques and in less time.

SUMMARY OF THE INVENTION

The preferred embodiment of the invention comprises a method and apparatus for optimizing dose delivery involving stereotactic computer techniques comprising: (a) determining an enclosing volume circumscribing a predetermined volume to be dosed; (b) meshing the enclosing volume with node points; (c) providing problem variables; (d) calculating the dose to be delivered to each of the node points; (e) formulating an objective function; (f) solving a numerical optimization algorithm minimizing the objective function; and (g) repeating (e) and (f) until the problem variables are optimized.

The preferred method and apparatus for determining an enclosing volume comprises: (a) graphically simulating a calculated tumor volume as the predetermined volume; (b) calculating the centroid and major axis dimensions of the calculated tumor volume; and (c) calculating and providing an enclosing volume with the centroid of the tumor volume at the center of the enclosing volume, the enclosing volume enclosing the tumor volume plus a nonpathologic margin.

The preferred method and apparatus for meshing the enclosing volume with node points comprises: (a) assigning three-dimensional coordinates to the node points; (b) determining the position of the node points relative to the predetermined volume; and (c) weighting the nodes according to their position.

The preferred apparatus and method for providing problem variables comprises (a) choosing isotopic seed activity; (b) orienting a catheter; (c) locating isotopic seeds along the catheter; and (d) setting upper and lower limits to the variables. The preferred apparatus and method for calculating the dose delivered to each of the node points comprises: (a) assigning three-dimensional coordinates to the isotopic seeds; and (b) calculating individual node doses by the equation:

$$D_i = \sum_{j=1}^{n_c} \left( \sum_{k=1}^{n_s} G_j(S_{jk}, r_{ik}) \right)$$

wherein:
i = current node number,
j = current catheter number,
k = current seed number,
$n_c$ = total number of catheters,
$n_s$ = total number of seeds per catheter,
$D_i$ = total radiation dose at node i, $\sum_{k=1}^{n_s} G_j(S_{jk}, r_{ik})$ = node radiation dose from catheter j, $S_{jk}$ = strength of seed k in catheter j, and
$r_{jk}$ = radius from seed k in catheter j to node i.

An alternative apparatus and method for providing problem variables comprises: (a) choosing a pattern of beam rotation relative to an isocenter; (b) selecting beam strength; (c) selecting beam collimation; and (d) setting upper and lower limits to the problem variables. The preferred apparatus and method for calculating the dose delivered to each of the node points comprises: (a) separating each beam path into a predetermined number of individual beams; and (b) calculating individual node doses by the equation:

$$D_i = \sum_{j=1}^{n_b} G_j(s_j, c_j, \overline{d_j})$$

wherein:
i = current node number,
j = current beam number,
$n_b$ = total radiation dose at node i,
$G_j(S_j, C_j, \overline{d_j})$ = node radiation dose from beam j,
$s_j$ = strength of beam j,
$c_j$ = collimation of beam j, and
$\overline{d_j}$ = direction of beam j.

The preferred apparatus and method for formulating the objective function comprises: (a) determining whether each node within the enclosing volume is dead or alive relative to a predetermined dose; (b) assigning each node to one of four specific subtotals, including (1) nodes inside the predetermined volume and alive, (2) nodes inside the predetermined volume and dead, (3) nodes outside the predetermined volume and alive, and (4) nodes outside the predetermined volume and dead; (c) dividing each of the specific subtotals by the total number of nodes; and (d) summing (1) the ratio of nodes outside the predetermined volume and dead and (2) the ratio of nodes inside the predetermined volume and alive. In this embodiment, the node error or tumor fit error objective function is minimized.

An alternative apparatus and method for formulating another objective function comprises assigning status factors to the nodes as follows: (1) a value of +P for nodes inside the predetermined volume and dead, (2) a value of −1 for nodes inside the predetermined volume and alive, (3) a value of −1 for nodes outside the predetermined volume
and dead, and (4) a value of 0 for nodes outside the predetermined volume and alive, wherein:

$$P = e^{-(D_i - D_e)^2} \delta^2$$

$D_i$ = Radiation dose at node
$D_o$ = Predetermined dose, and
$\delta$ = decay factor.

This embodiment for solving the numerical optimization algorithm comprises maximizing the node status objective function.

A primary object of the present invention is to provide optimization of dose delivery in various treatments, such as treatment of brain tumors.

A further object of the present invention is to maximize dose delivery in pathologic tissue while minimizing dosage in nonpathologic tissue.

An advantage of the present invention is that dose delivery systems can be employed with diverse therapies.

Yet another advantage of the present invention is the extremely rapid solution of the dosage delivery problem.

Other objects, advantages and novel features, and further scope of applicability of the present invention will be set forth in part in the detailed description to follow, taken in conjunction with the accompanying drawing, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention.

DETAILED DESCRIPTION OF THE PREFERRED EMBODIMENTS OF THE INVENTION

The present invention relates generally to the optimization of a dose delivery system. Specifically, the dose to be delivered can be any dosing agent or physical phenomena, such as radiation, poisons, chemical compounds, hypothermia compounds, hyperthermia compounds, antimatter, in the form of antiprotons, photosensitive compounds, and the like. The invention is not limited to the dosing agents listed above, as the optimization techniques of the invention may be used with a variety of dosing agents and treatment plans. The invention is particularly useful for the radiation treatment of brain tumors using stereotactic techniques and thus the detailed description below is directed to such techniques and thus the detailed description below is directed to such treatment. Although the use of a stereotactic frame and brachytherapy catheters are discussed herein, other reference frames and other dose delivery systems may also be used in accordance with the invention.

FIGS. 1-4 depict a tumor volume 10 calculated and graphically simulated. Methods for simulating the tumor volume 10 are disclosed in parent application Ser. No. 07/500,788, although other simulation methods which might be available can also be employed. Centroid 11 and major axis 12 of tumor volume 10 are calculated. Depending upon the dose delivery system contemplated, line 13 could comprise, e.g., the center line of brachytherapy catheter bundle 14 or the center beam of a major beam path employed in external beam radiation therapy.

Figure 1:
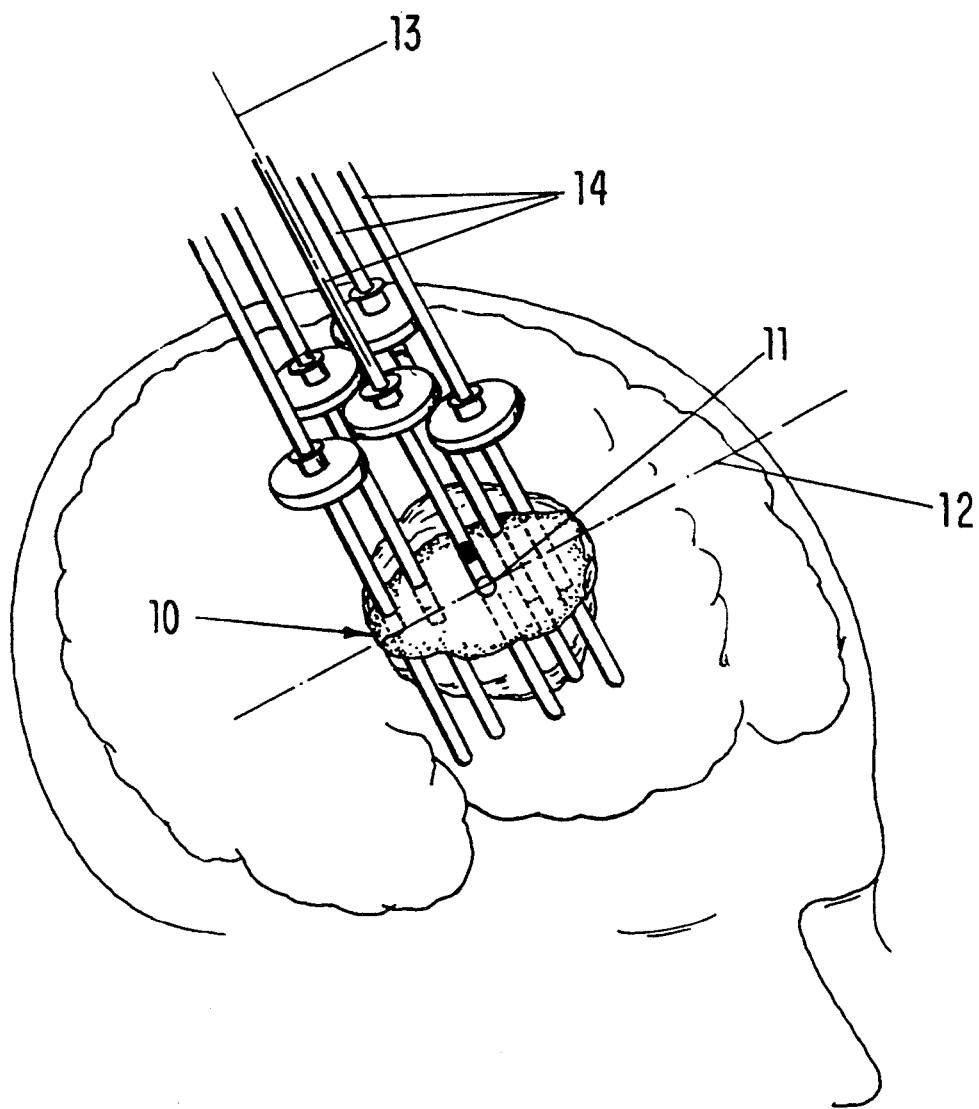
FIG. 1 is a perspective view of a form of a dose delivery system showing a simulated tumor volume, brachytherapy catheters, and radioisotope seeds.
Figure 2:
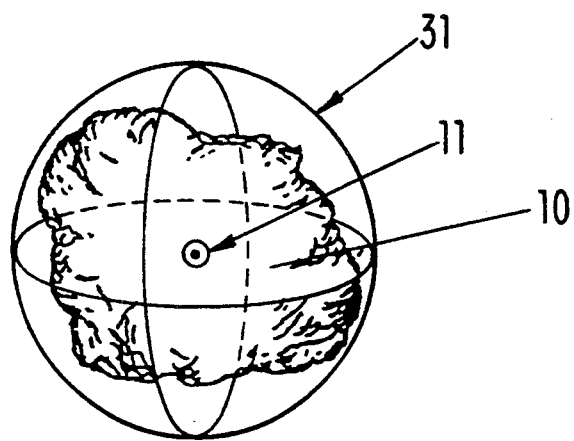
FIG. 2 is a perspective view of a simulated enclosing volume circumscribing the simulated tumor volume of FIG. 1.
Figure 3:
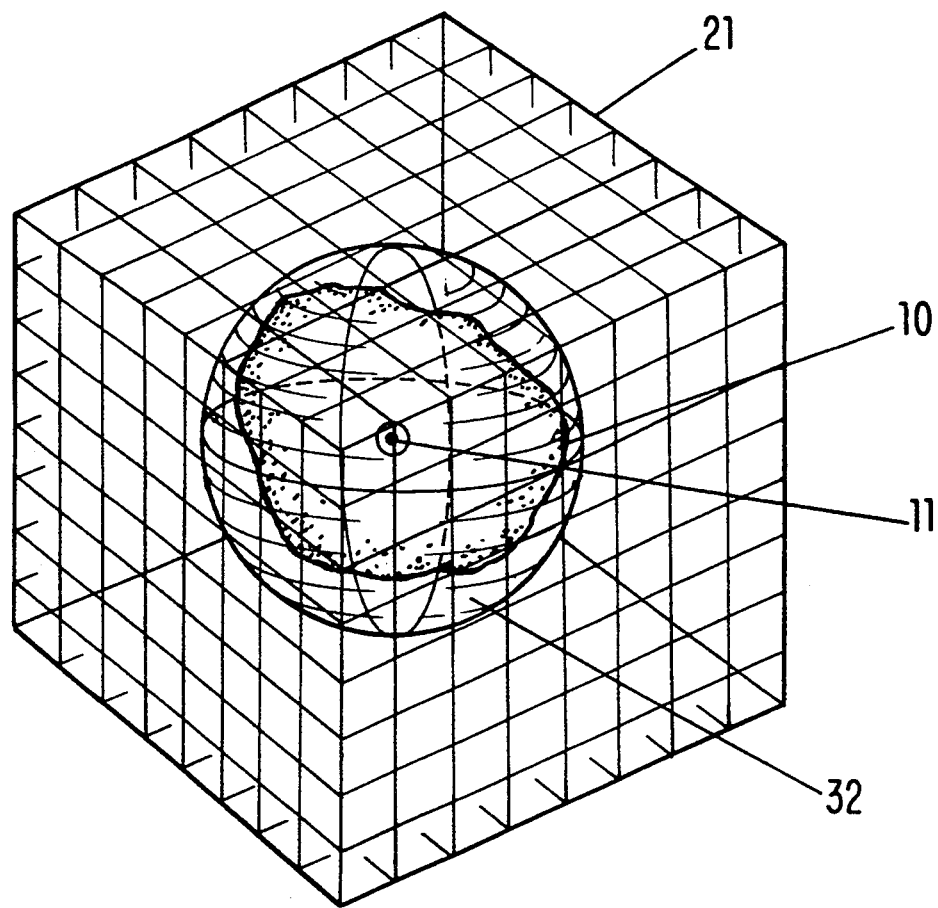
FIG. 3 is a perspective view of the enclosing volume and tumor volume of FIGS. 1 and 2 meshed with node points.
Figure 4:
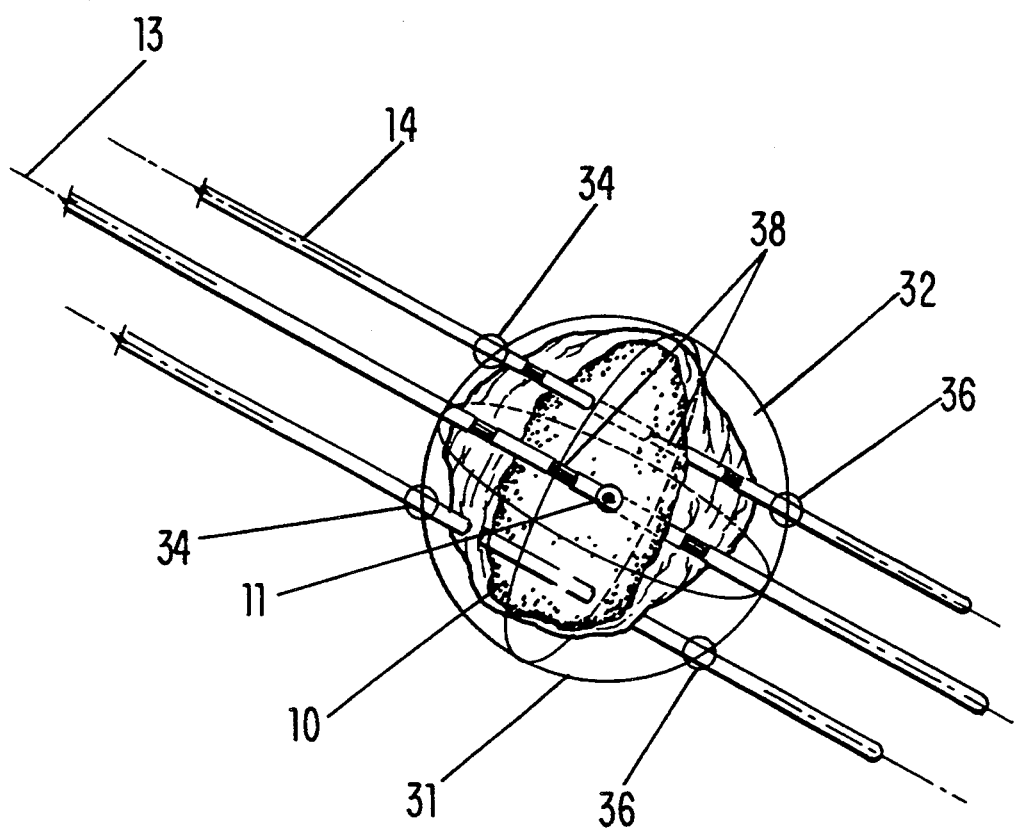
FIG. 4 is a perspective view of parametric seed positioning relative to the enclosing volume and tumor volume of FIGS. 1 and 2.

An enclosing volume 21 is calculated with tumor volume centroid 11 at the center of such volume. The preferred configuration for volume 21 is a cube, but other geometric shapes, such as a sphere, as shown in FIGS. 2-4, may be employed. A volume which will enclose tumor volume 10 is chosen such that a predetermined nonpathologic margin 32 of presumably healthy tissue is created. This margin is variable depending upon the dose delivery system employed. Normally, a higher percentage of healthy tissue margin is required for external beam radiation therapy to better track the dose deposited in the nonpathologic tissue.

Subsequent to calculation of the enclosing volume, enclosing volume 21 is meshed with a plurality of node points, as depicted by the mesh intersections in FIG. 3. The number of node points is variable depending upon mesh dimensions, desired accuracy, and computation time available. A determination is then made as to whether each node point is within or without tumor volume 10. This is accomplished by determining the size of each voxol according to the dimension of the mesh and the number of nodes defined; determining the distinct stereotactic frame coordinates (x, y, and z) of each of these nodes; determining whether each node is located within or without tumor volume 10; and flagging each node accordingly (0 or 1).

Initially there are some values or variables that must be chosen by the user (e.g., physician, surgeon, or technician) to start the optimization process. For brachytherapy or radioisotopic seed used, the number of seeds per catheter, the configuration of the catheters within the available catheter block hole pattern, and the dose delivery time. Treatment planning may further include choosing radioisotope seed type (e.g., I-125, irridtum, or the like) and radioactivity level; using a nomogram to obtain a preliminary number and spacing of seeds relative to a given tumor volume; a computerized numerical optimization program to "best fit" radioisotopic seeds to the given tumor volume; visually inspecting graphically simulated dose zone delivery within the tumor volume; and confirming or adjusting the constraints of the computerized numerical optimization program.

For external beam radiation therapy, the values or variables include the number of isocenters to be used and the location of the isocenters within the tumor. Treatment planning may further dictate determination of collimator size and shape and a preliminary number of isocenters for radiation beam delivery; a computerized numerical optimization program to "best fit" intended dose to tumor volume, visually inspecting graphically simulated dose zone delivery within the tumor volume, and confirming or adjusting the constraints of the computerized numerical optimization program.

Figure 5:
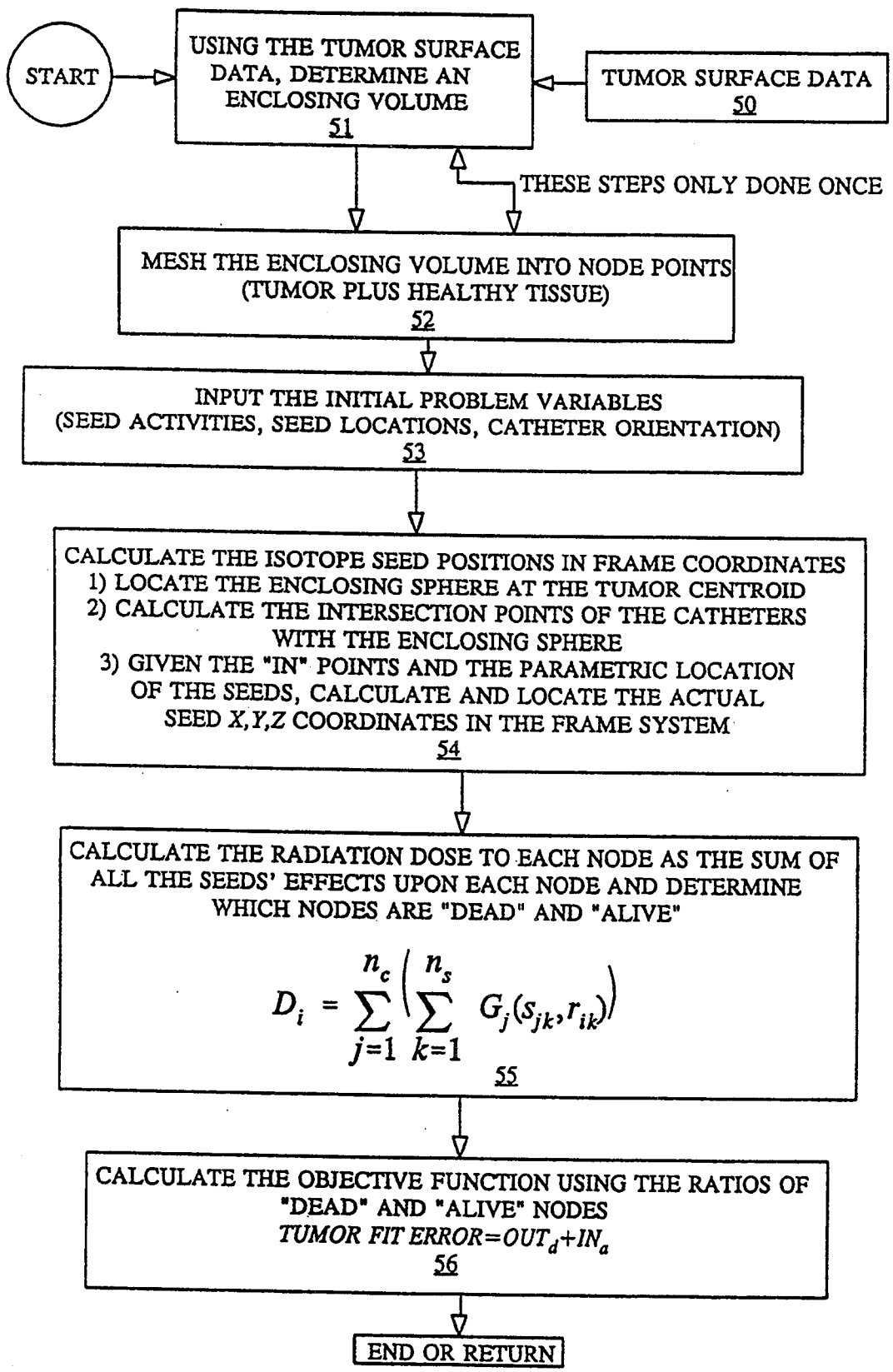
FIG. 5 is a flow diagram of the calculation of the tumor fit error (objective) function of the present invention useful for brachytherapy.

With specific reference to FIG. 5, the preferred initial treatment method for use of the invention for brachytherapy comprises the following steps: Tumor surface data 10 is obtained 50. This tumor surface data 10 is used to determine 51 an enclosing volume 21, such as shown in FIG. 3. The enclosing volume 21 is meshed into node points (tumor plus healthy tissue) 52, such as shown in FIG. 3. Initial problem variables, such as choosing the initial individual seed activity, the initial orientation of the catheter bundle and the initial location of the seeds along each catheter, are input 53. Providing the initial treatment plan or design may be done automatically using a nomogram incorporated into the software or input by the user. The initial treatment plan or design is used as a starting point for the optimization algorithm of the invention. The performance of the optimization algorithm is not all that sensitive to the initial design; however, it should be noted that poor initial input requires the optimization algorithm to look harder and longer for the optimal design. Upper and lower bounds on the design variables are either arbitrarily set or set to remain within available bounds (e.g., a chosen type of isotope seed will have a certain activity range in which it is available).

The isotope seed positions are then calculated and located 54 in x, y, and z frame coordinates. The orientation of the catheter bundle is defined by two rotation angles about the x and y axes respectively. Depending on the stereotactic frame design, the stereotactic frame may be positioned in such a way that the center of its rotation angles coincides or intersects with the centroid 11 of the tumor 10. This allows the centroid line 13 of the catheter bundle 14 to intersect with the tumor centroid 11 (see FIG. 1). An enclosing cube or other volume 21 is then located with its center at the tumor centroid 11 and a sphere with a radius just large enough to totally enclose the tumor volume, as in FIG. 3. Knowing the radius of the sphere and the catheter pattern, the intersection points of each catheter with the enclosing sphere 31 and the length of each catheter within the sphere 31 can easily be calculated. Since the lengths of each catheter enclosed within the sphere 31 will remain constant as the bundle 14 orientation angles are varied, these lengths can be used to parametrically locate the radioisotope seeds along the catheter. This is done by designating the entrance points 34 of each catheter into the enclosing volume 21 as a "0" in parametric space, and the exit points 36 as "1". Therefore, a number between 0 and 1 for a specific seed 38 along one of the catheters can be used to uniquely define its x, y, and z coordinates in the frame system. This concept is represented as a two-dimensional view in FIG. 4. This parametric location process using an enclosing sphere 31 (or other volume) is implemented for two reasons: (1) to reduce the number of design variables (there is only one location variable for each seed, instead of its actual x, y, and z, coordinates), and (2) to insure that the relationship between the catheter bundle orientation angles and the seed positioning would remain decoupled when using a parametric location scheme.

Given the x, y, z coordinates of each isotope seed, the radiation dose to each individual node within the meshed volume can be calculated 55 as the sum of each seeds dose contribution to that particular node location (see Equation 1).

$$D_i = \sum_{j=1}^{n_c} \left( \sum_{k=1}^{n_s} G_j(s_{jk}, r_{ik}) \right) \quad (1)$$

where:
i = current node number
j = current catheter number
k = current seed number
$n_c$ = total number of catheters
$n_s$ = total number of seeds per catheter
$D_i$ = total radiation dose at node i $\sum_{k=1}^{n_s} G_j(S_{jk}, r_{ik})$ = node radiation dose from catheter j $S_{jk}$ = strength of seed k in catheter j
$r_{jk}$ = radius from seed k in catheter j to node
The calculated dose received by each node in the meshed volume can be used in a number of ways to evaluate the "goodness" of the current treatment plan.

Given the dose calculated at each node, it is determined whether each individual node within the meshed volume is "dead" or "alive" based on a predetermined "kill" dose of radiation. As each node 31 is inquired, that node is recorded as "dead" or "alive" by adding a "1" to the values of various subtotals. The four subtotals are identified as: (1) the number of nodes inside the tumor and alive; (2) the number of nodes inside the tumor and dead; (3) the number of nodes outside the tumor and alive; and (4) the number of nodes outside the tumor and dead.

Figure 6:
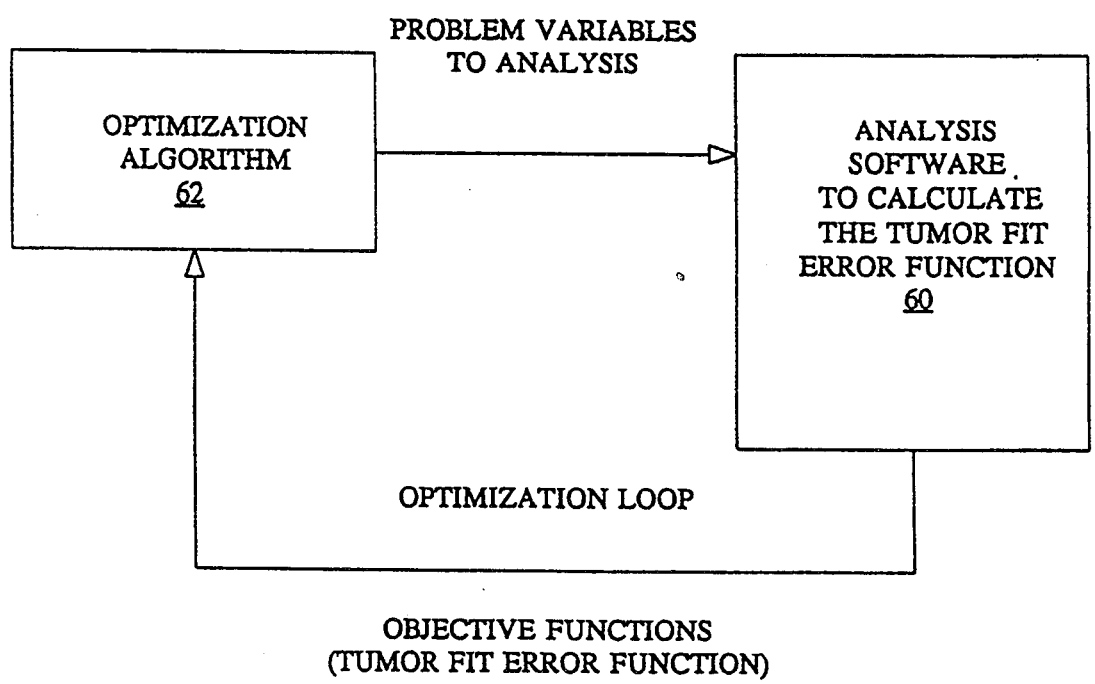
FIG. 6 is a flow chart of the optimization loop of the invention.

Using the information stored in the subtotals, the "dead" and "alive" ratios are calculated by dividing the number in each bin by the total number of nodes. These ratios are then combined to formulate 56 an objective function for the optimization process. This objective function for tumors is referred to herein as "tumor fit error" value. It is defined as the sum of the ratio of nodes outside the tumor and dead, plus the ratio of nodes inside the tumor and alive (see Equation 2).

$$\text{Tumor Fit Error} = \text{Out}_d + \text{In}_a \quad (2)$$

where:
Out$_d$ = Ratio of nodes outside the tumor and dead
In$_a$ = Ratio of nodes inside the tumor and alive As shown in FIG. 6, when a value of tumor fit error is obtained 60 for the current seed placement and bundle orientation, a numerical optimization algorithm (e.g., Generalized Reduced Gradient or Sequential Quadratic Programming) is then used 62 to determine the optimal seed placement, activity and bundle orientation. Obviously, as the tumor fit error value approaches zero, the radiation kill zone created by the isotope seeds approaches the actual shape of the tumor. Therefore, the optimization problem can be stated: "Minimize the tumor fit error such that all nodes inside the tumor are dead." As shown in FIG. 6, the optimization algorithm iterates through a number of designs by perturbing the variable values (seed location, strength, bundle orientation, and other associated variables) and executing these steps until it reaches the best combination of variables to minimize the tumor fit error.

Figure 7:
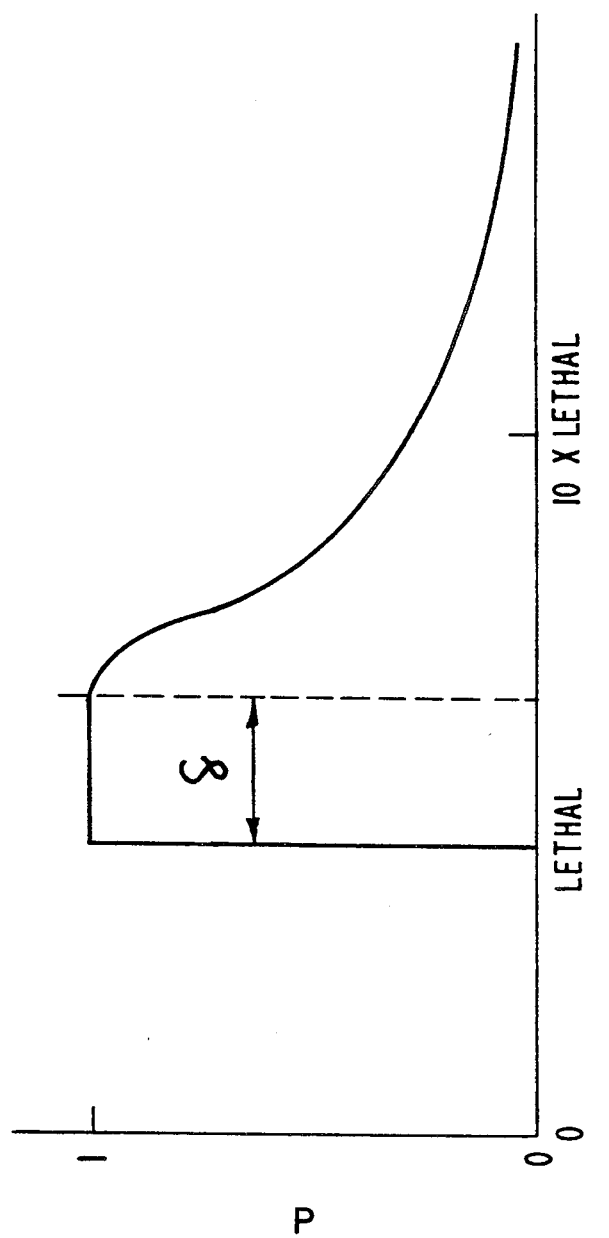
FIG. 7 is a graph showing a curve of the "inside and dead" overkill penalty function of the present invention.

With specific reference to FIG. 7, an alternative brachytherapy dose delivery method designed to provide homogeneous dose delivery comprises assigning status factors as follows:

Calculate the individual node radiation doses in the same manner as detailed above. By comparing against the predetermined "kill" dose, decide if the node is "dead" or "alive" and assign it a status factor as defined below.

If the node is:
Inside the tumor and dead, assign the node as +P
Inside the tumor and alive, assign the node as −1
Outside the tumor and dead, assign the node as −1
Outside the tumor and alive, assign the node as 0
where:

$$P = e^{-(D_i - D_e)^2 / \delta^2} \quad (3)$$

$D_i$ = Radiation dose at node i
$D_o$ = Predetermined lethal radiation dose
$\delta$ = decay factor of the overkill penalty The P function is used to define an "overkill" penalty to a node inside the tumor with a dose above that of the lethal dose; that is, when the dose level is below the lethal dose, the value of P is zero, but as it passes the lethal dose, its value jumps to 1 and then starts to decrease as the node dose level increases above the lethal limit. The parameter $\delta$ is used to change the amount of dwell nearer to a P value of 1 before the exponential decay becomes effective and quickly decreases the "utility" of an inside node that has been overkilled. As can be seen, only the nodes that are inside and dead receive a factor greater than zero with the undesirable conditions of inside and alive and outside and dead being assigned negative status factors.

After assigning a status factor to each node, an objective function for the optimization process can be formed 60 by summing all of the node status factors (see Equation 3). This "tumor status" objective function will be different for each seed placement design and would reach its maximum when there are few "outside dead" and "inside alive" nodes and most of the "inside dead" nodes have a status factor of 1 (meaning they have just attained a level of "dead"). Notice that maximizing the "tumor status" function will have the effect of homogenizing the dose distribution within the tumor boundaries because the maximum value of the node status factor is assigned only to those nodes that are not "overkilled" by too much. Therefore, the optimization problem can be stated: "Maximize the tumor status function." Insuring that all the nodes inside are dead could be accomplished by increasing the negative value of the "inside alive" status factor and more heavily penalizing the "tumor status" function when "inside alive" nodes exist. The optimization algorithm will iterate through a number of designs or treatment plans by perturbing the variable values (seed location, strength, bundle orientation, and other associated variables) until it reaches the best combination of variables to maximize the "tumor status" function.

Figure 8:
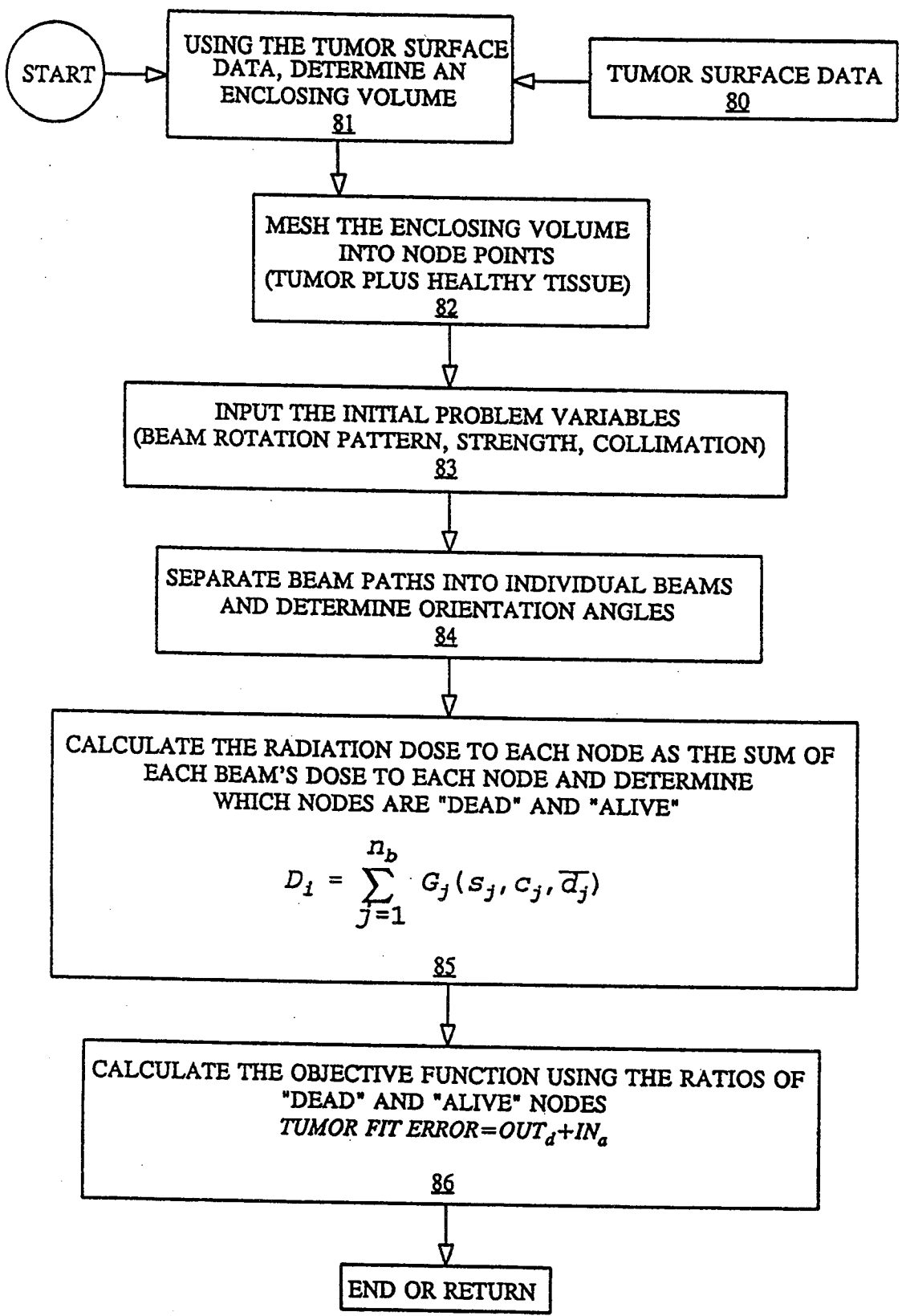
FIG. 8 is a flow diagram of the calculation of the tumor fit error function of the present invention useful for external beam radiation.

Employment of external beam radiotherapy also requires an initial design or treatment plan comprising problem variables. With specific reference to FIG. 8, and as in FIG. 5, tumor surface data is obtained 80, which is used to determine 81 an enclosing volume. Initial program variables are chosen and input 82. These program variables include a pattern of beam rotation for each isocenter, the beam strength and beam collimation (either or both of the last two could be provided as a function of beam rotation with the variables then becoming the coefficients of polynomial functions or control points of Bezier curves). An initial treatment plan appropriate for this type of therapy is used as a starting point for the optimization algorithm. The performance of the optimization algorithm is not all that sensitive to the initial treatment plan; however, it should be noted that poor initial input will again require the optimization algorithm to look harder and longer for the optimal design. Upper and lower bounds on the design variables are either arbitrarily set or set to remain within available bounds (e.g., a beam rotation pattern may be constrained to remain between certain angles to avoid sensitive areas of the brain).

Each major beam path within each isocenter's application pattern is separated 84 into a predetermined number of individual beams. This is done so that the actual continuous beam paths can be approximated and evaluated by the dose function.

Given the orientation angles (direction cosines) of each discrete beam, the radiation dose to each individual node is calculated 85 within the meshed volume by summing each beam's dose contribution to each node as follows:

$$D_i = \sum_{j=1}^{n_b} G_j(s_j, c_j, \overline{d_j}) \quad (4)$$

where:
i = current node number
j = current beam number
$n_b$ = total number of beams
$D_i$ = total radiation dose at node i
$G_j(s_j, c_j, \overline{d_j})$ = node radiation dose from beam j
$s_j$ = strength of beam j
$c_j$ = collimation of beam j
$\overline{d_j}$ = direction of beam j The objective function (e.g., tumor fit function) is formulated 86 as discussed above. Given the dose calculated at each node, it is determined whether each individual node within the meshed volume is "dead" or "alive" based on a predetermined "kill" dose of radiation. As each node is inquired, that node is recorded as "dead" or "alive" by adding a "1" to the values of various collection subtotals. The four subtotals identified are: (1) the number of nodes inside the tumor and alive; (2) the number of nodes inside the tumor and dead; (3) the number of nodes outside the tumor and alive; and (4) the number of nodes outside the tumor and dead.

Using the information stored in the subtotals, the "dead" and "alive" ratios are calculated by dividing the number in each subtotal by the total number of nodes. These ratios are then combined to form an objective function for the optimization process. This objective function for tumors is referred to herein as the "tumor fit error" value. It is defined as the sum of the ratio of nodes outside the tumor and dead, plus the ratio of nodes inside the tumor and alive (see Equation 5).

$$\text{Tumor Fit Error} = \text{Out}_d + \text{In}_a \qquad (5)$$

where:

$\text{Out}_d$ = Ratio of nodes outside the tumor and dead $\text{In}_a$ = Ratio of nodes inside the tumor and alive When a tumor fit error value is obtained for the given beam variables and isocenters, a numerical optimization algorithm (e.g., Generalized Reduced Gradient or Sequential Quadratic Programming algorithms) is used to determine the optimal combination of beam variables. As the tumor fit error value approaches zero the radiation kill zone created by the beam trajectories approaches the actual shape of the tumor. Therefore, the optimization problem can be stated: "Minimize the tumor fit error such that all nodes inside the tumor are dead." Again, as shown in FIG. 6, the optimization algorithm iterates through a number of designs by perturbing the variable values (beam rotation pattern, strength, and collimation, and other associated variables) until it reaches the best combination of variables to minimize the tumor fit error.

Alternatively, a homogeneous dose delivery method can also be used with external beam radiotherapy using status factors, as previously discussed.

The apparatus can further comprise structure for simulating a brain probe and structure for simulating manipulation of the probe within a video presentation; structure for simulating one or more electrodes and for simulating manipulation of electrodes within a video presentation. Additionally, it can comprise structure for storing representations of physiological response points and for selectively recalling and displaying any of the response points within a video presentation. The apparatus can further comprise structure for providing stereotactic coordinates for a user selected point on a video presentation.

Figure 9:
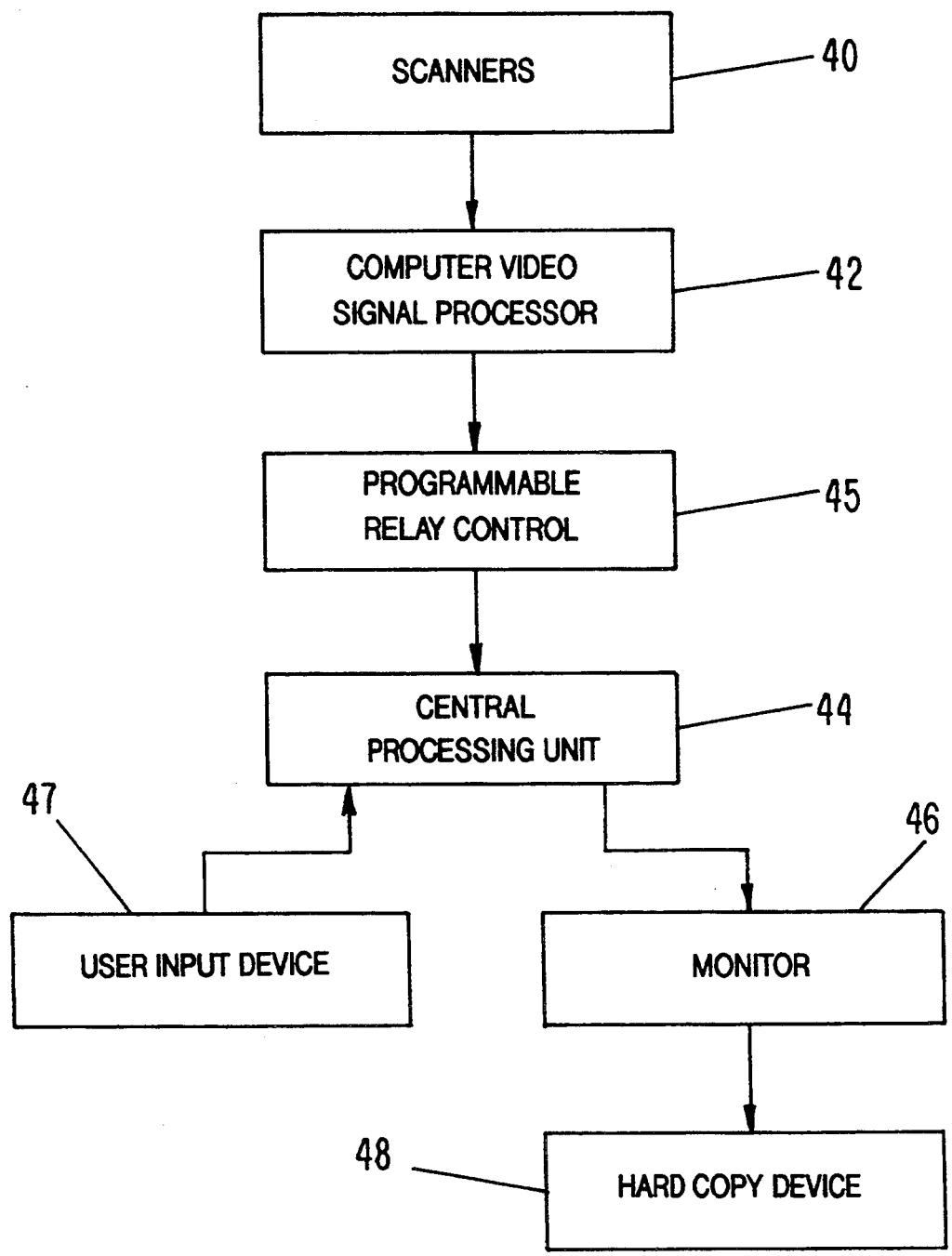
FIG. 9 is a preferred hardware block diagram in accordance with the invention.

With reference to FIG. 9, the image acquiring structure preferably comprises structure for acquiring an image from a CT scanner, an NMR scanner, a PET scanner, an X-ray scanner, a DSA scanner and/or an isotope scanner 40. This scanning data, which is in various, typically non-standard formats, is convertible to a standard format using a PROM computer video signal processor 42. The converted scanning data is made available, through programmable relay control 45, to a central processing unit (CPU) 44, preferably comprising hard disc storage, floppy disc storage, streamer tape storage, and high-resolution frame grabber with a high speed graphics and video image processor. The image acquisition structure is preferably uniquely programmable to acquire any of a predetermined number of image types. The apparatus preferably further comprises structure providing for user to input 47 within a sterile environment, connected to CPU 44 such as an infrared grid disposed across the image displaying screen, such as monitor 46. The apparatus preferably further comprises structure for measuring distances, volumes and areas within an actual patient's brain. The apparatus further preferably comprises structure for generating a simulated three-dimensional image of the actual patient's brain, the simulated three-dimensional image preferably being representative of a CT image, an NMR image, a PET image, a DSA image, isotope or an X-ray image. The image can comprise a composite of images from more than one source. The apparatus can further comprise simulated three-dimensional images comprised of a composite of images from more than one source. The apparatus can further comprise structure for determining optimum placement or dosage for an isodose implantation. A recording or archiving device, such as hard copy device 48, for storing user procedure can be provided.

Figure 10:
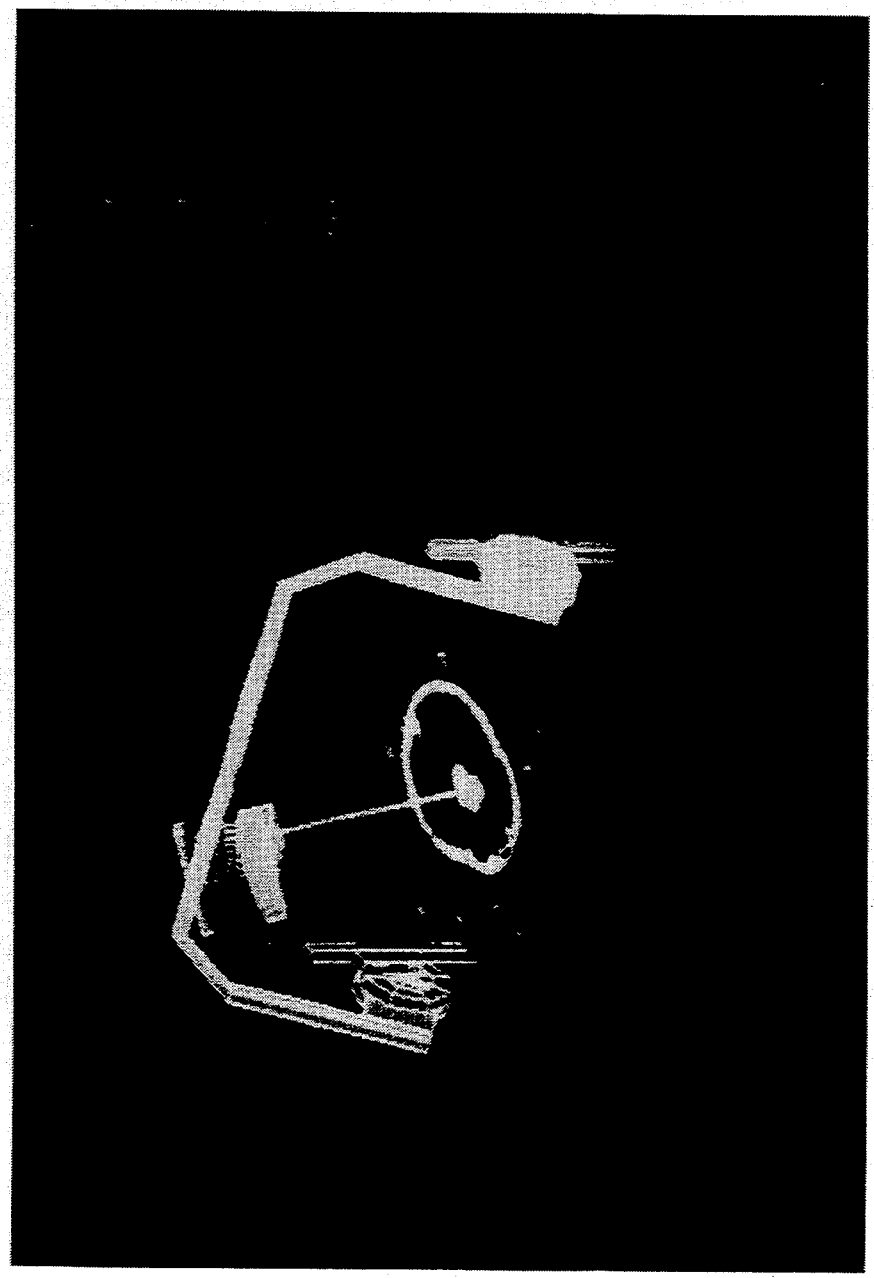
FIG. 10 is a photograph of a computer screen display of an actual CT image section or scan slice combined with a stereotactic frame and a stereotactic surgical probe directed towards a tumor lesion within the confines of the head.

FIG. 10 shows an actual CT scan planar slice simulated within a stereotactic frame with a stereotactic surgical probe directed towards a tumor lesion within the confines of the head.

As discussed above, the computerized numerical optimization dose delivery methods herein disclosed are also suitable for other dose delivery methods and devices including thermal or cryogenic probes, infrared or laser systems, chemical doses, drug diffusion systems, and, ultimately, antimatter in the form of antiprotons.

Additionally, other modifications may be made to the optimal dose delivery system of the invention. These are discussed below.

Weighting of nodes in sensitive brain areas may exert greater influence on the objective function, thereby lessening dosage on such nodes. Such capability could be directly tied to brain map databases, such as disclosed in co-pending application Ser. No. 07/290,316.

In an alternative embodiment, increasing node density near the tumor boundaries while decreasing node density near the tumor center and boundaries of the enclosing volume also improves "best fit" of kill zone to tumor volume, thereby increasing the accuracy of the treatment.

Use of artificial intelligence rule bases in conjunction with the optimization algorithms allows more flexibility in defining the optimization process. For example, artificial intelligence can be used to allow the number of catheters and their layout pattern to be variables in brachytherapy optimization. This occurs because the actual solution method changes as the number of catheters and their pattern changes. This integration of artificial intelligence into the numerical optimization process allows current parameters which are entered as constants to the equations to be given a desired range ("limited variables").

Real-time three dimensional (3-D) visualization of the optimization process can be incorporated. The radiation treatment planner can watch the dose distribution change to fit the tumor volume. This permits even greater flexibility in the planning process, allowing the treatment planner to stop the process at any point during the optimization, possibly adjust "problem variables" as appropriate, and re-start the optimization process with the new entries.

Three dimensional simulation of dose-volume histograms can be presented to the user in a fashion such that the user can simultaneously perceive the tumor volume in relationship to a 3-D rendition of a dose-volume histogram of dosimetry to surrounding tissue.

Currently there are no highly accurate methods of determining actual tumor boundaries; use of radioisotope or other such tagging or identification techniques in conjunction with imaging and graphics techniques, such as disclosed in co-pending applications, helps to better define the actual tumor margin.

Although the invention has been described with reference to these preferred embodiments, other embodiments can achieve the same results. Variations and modifications of the present invention will be obvious to those skilled in the art and it is intended to cover the appended claims all such modifications and equivalents.

What is claimed is:

1. A method of optimizing dose delivery involving stereotactic computer techniques comprising the steps of:
   1) generating and displaying graphic simulation of a predetermined volume to be dosed from image data obtained from at least one of a plurality of imaging scanners;
   2) providing a stereotactic device and thereby establishing three-dimensional coordinates about the predetermined volume to be dosed;
   3) determining an enclosing volume circumscribing said predetermined volume to be dosed;
   4) meshing said enclosing volume with node points;
   5) providing problem variables relating to dosage;
   6) calculating the dose to be delivered to each of said node points;
   7) formulating an objective function for evaluating the dosage;
   8) solving a numerical optimization algorithm optimizing the objective function;
   9) repeating steps 7 and 8 until said problem variables are optimized; and
   wherein the step of determining an enclosing volume circumscribing the predetermined volume to be dosed further comprises the steps of:
   1) graphically simulating a calculated volume as said predetermined volume;
   2) calculating the centroid of said calculated volume; and
   3) calculating and providing an enclosing volume with said centroid of said calculated volume at the center of the enclosing volume, said enclosing volume enclosing said calculated volume.

2. The method of claim 1 wherein the step of determining an enclosing volume additionally comprises the step of calculating a major axis dimension of said calculated volume.

3. The method of claim 1 wherein the step of meshing said enclosing volume with node points comprises the steps of:
   a. assigning three-dimensional stereotactic device coordinates to said node points;
   b. determining the position of said node points relative to said predetermined volume; and
   c. weighting said dose according to their position.

4. The method of claim 1 wherein said step of providing problem variables comprises the steps of:
   a. choosing isotopic seed activity;
   b. orienting a catheter;
   c. locating isotopic seeds along the catheter; and
   d. setting upper and lower limits to said variables.

5. The method of claim 4 wherein said step of calculating the dose delivered to each of said node points comprises the steps of:
   a. assigning three-dimensional stereotactic device coordinates to the isotopic seeds; and
   b. calculating individual node doses by the equation $$D_i = \sum_{j=1}^{n_c} \left( \sum_{k=1}^{n_s} G_j(s_{jk}, r_{ik}) \right)$$

wherein:
   i = current node number,
   j = current catheter number,
   k = current seed number,
   $n_c$ = total number of catheters,
   $n_s$ = total number of seeds per catheter,
   $D_1$ = total radiation dose at node i, $$\sum_{k=1}^{n_s} G_j(S_{jk}, r_i) = \text{node radiation dose from catheter } j,$$

$s_{jk}$ = strength of seed k in catheter j, and
   $r_{jk}$ = radius from seed k in catheter j to node i.

6. The method of claim 1 wherein said step of providing problem variables comprises the steps of:
   a. choosing a pattern of beam rotation relative to an isocenter;
   b. selecting beam strength;
   c. selecting beam collimation; and
   d. setting upper and lower limits to said problem variables.

7. The method of claim 6 wherein the step of calculating the does delivered to each of said node points comprises the steps of:
   a. separating each beam path into a predetermined number of individual beams; and
   b. calculating individual node doses by the equation $$D_i = \sum_{j=1}^{n_b} G_j(s_j, c_j, \bar{d}_j)$$

wherein
   i = current node number,
   j = current catheter number,
   $n_b$ = total number of beams,
   $D_1$ = total radiation dose at node i,
   $G_j(S_j, C_j, \bar{d}_j)$ = node radiation does from beam j,
   $s_j$ = strength of beam j,
   $c_j$ = collimation of beam j, and
   $\bar{d}_j$ = direction of beam j.

8. The method of claim 1 wherein the step of formulating an objective function comprises the steps of:
   a. determining whether each said node within said enclosing volume is dead or alive relative to a predetermined dose;
   b. assigning each said node to one of four specific subtotals, including (1) nodes inside the predetermined volume and alive, (2) nodes inside the predetermined volume and dead, (3) nodes outside the predetermined volume and alive, and (4) nodes outside the predetermined volume and alive, and (4) nodes outside the predetermined volume and dead;

c. dividing each of said specific subtotals by the total number of nodes; and d. summing (1) the ratio of nodes outside the predetermined volume and dead and (2) the ratio of nodes inside the predetermined volume and alive.

9. The method of claim 1 wherein the step of formulating an objective function comprises the step of assigning status factors to the nodes as follows: (1) a value of $+P$ for nodes inside the predetermined volume and dead, (2) a value of $-1$ for nodes inside the predetermines volume and alive, (3) a value of $-1$ for nodes outside the predetermined volume and dead, and (4) a value of 0 for nodes outside the predetermined volume and alive, wherein:

$$P = e^{-(D_i D_o)^2/\delta^2}$$

$D_i$ = Radiation dose at node i,
$D_o$ = Predetermined dose, and
$\delta$ = decay factor.

10. An apparatus for optimizing dose delivery involving stereotactic computer techniques comprising:
   means for generating and displaying graphic simulation of a predetermined volume to be dosed from image data obtained from at least one of a plurality of imaging scanners;
   stereotactic device means for establishing three-dimensional coordinates about the predetermined volume to be dosed;
   means for determining an enclosing volume circumscribing said predetermined volume to be dosed;
   means for meshing said enclosing volume with node points;
   means for providing problem variables relating to dosage;
   means for calculating the dose to be delivered to each of said node points;
   means for formulating an objective function for evaluating the dosage;
   means for solving a numerical optimization algorithm optimizing the objective function; and
wherein said means for determining an enclosing volume circumscribing the predetermined volume to be dosed comprises:
   means for graphically simulating a calculated volume as said predetermined volume;
   means for calculating the centroid of said calculated volume; and
   means for calculating and providing an enclosing volume with said centroid of said calculated volume at the center of the enclosing volume, said enclosing volume enclosing said calculated volume.

11. The method of claim 10 wherein said means for determining an enclosing volume additionally comprises means for calculating a major axis dimension of said calculated volume.

12. The method of claim 10 wherein said means for meshing said enclosing volume with node points comprises:
   means for assigning three-dimensional stereotactic device coordinates to said node points;
   means for determining the position of said node points relative to said predetermined volume; and
   means for weighting said dose according to their position.

13. The method of claim 10 wherein said means for providing problem variable comprises:

means for choosing isotopic seed activity;
   means for orienting a catheter;
   means for locating isotopic seeds along the catheter; and
   means for setting upper and lower limits to said variables.

14. The method of claim 13 wherein said means for calculating the dose delivered to each of said node points comprises:
   means for assigning three-dimensional stereotactic device coordinates to the isotopic seeds; and
   means for calculating individual node doses by the equation $$D_i = \sum_{j=1}^{n_c} \left( \sum_{k=1}^{n_s} G_j(S_{jk}, r_{ik}) \right)$$

wherein:
   i = current node number,
   j = current catheter number,
   k = current seed number,
   $n_c$ = total number of catheters,
   $n_s$ = total number of seeds per catheter,
   $D_1$ = total radiation dose at node i, $$\sum_{k=1}^{n_s} G_j(S_{jk}, r_i) = \text{node radiation dose from catheter } j,$$

$s_{jk}$ = strength of seed k in catheter j, and
   $r_{jk}$ = radius from seed k in catheter j to node i.

15. The method of claim 10 wherein said means for providing problem variables comprises:
   means for choosing a pattern of beam rotation relative to an isocenter;
   means for selecting beam strength;
   means for selecting beam collimation; and
   means for setting upper and lower limits to said problem variables.

16. The method of claim 15 wherein said means for calculating the dose delivered to each of said node points comprises:
   means for separating each beam path into a predetermined number of individual beams; and
   means for calculating individual node doses by the equation $$D_i = \sum_{j=1}^{n_b} G_j(s_j, c_j, \overline{d_j})$$

wherein
   i = current node number,
   j = current beam number,
   $n_b$ = total number of beams,
   $D_1$ = total radiation dose at node i,
   $G_j(S_j, C_j, \overline{d_j})$ = node radiation dose from beam j,
   $s_j$ = strength of beam j,
   $c_j$ = collimation of beam j, and
   $\overline{d_j}$ = direction of beam j.

17. The method of claim 10 wherein said means for formulating an objective function comprises:
   means for determining whether each said node within said enclosing volume is dead or alive relative to a predetermined dose;

means for assigning each said node to one of four specific subtotals, including (1) nodes inside the predetermined volume and alive, (2) nodes inside the predetermined volume and dead, (3) nodes outside the predetermined volume and alive, and (4) nodes outside the predetermined volume and dead;

means for dividing each of said specific subtotals by the total number of nodes; and means for summing (1) the ratio of nodes outside the predetermined volume and dead and (2) the ratio of nodes inside the predetermined volume and alive.

18. The method of claim 10 wherein the means for formulating an objective function comprises the step of assigning status factors to the nodes as follows: (1) a value of $+P$ for nodes inside the predetermined volume and dead, (2) a value of $-1$ for nodes inside the predetermined volume and alive, (3) a value of $-1$ for nodes outside the predetermined volume and dead, and (4) a value of 0 for nodes outside the predetermined volume and alive, wherein:

$$P = e^{-(D_i D_o)^2/\delta^2}$$

$D_i$ = Radiation dose at node i,
$D_o$ = Predetermined dose, and
$\delta$ = decay factor.

* * * * *